(12) United States Patent
Cope et al.

(10) Patent No.: US 7,291,494 B2
(45) Date of Patent: *Nov. 6, 2007

(54) REGULATION OF TARGET PROTEIN ACTIVITY THROUGH MODIFIER PROTEINS

(75) Inventors: Gregory Cope, Pasadena, CA (US); Rati Verma, Pasadena, CA (US); Lakshminarayanan Aravind, Bethesda, MD (US); Eugene V. Koonin, Bethesda, MD (US); Raymond Deshaies, Claremont, CA (US); Xavier Ambroggio, Pasadena, CA (US)

(73) Assignees: California Institute of Technology, Pasadena, CA (US); National Institutes of Health, Bethesda, MD (US)

( * ) Notice: Subject to any disclaimer, the term of this patent is extended or adjusted under 35 U.S.C. 154(b) by 512 days.

This patent is subject to a terminal disclaimer.

(21) Appl. No.: 10/047,253

(22) Filed: Jan. 14, 2002

(65) Prior Publication Data

US 2003/0166243 A1   Sep. 4, 2003

Related U.S. Application Data

(60) Provisional application No. 60/322,322, filed on Sep. 14, 2001, provisional application No. 60/322,030, filed on Sep. 14, 2001, provisional application No. 60/261,314, filed on Jan. 12, 2001.

(51) Int. Cl.
| | |
|---|---|
| *C12N 9/48* | (2006.01) |
| *C12N 9/00* | (2006.01) |
| *C12Q 1/00* | (2006.01) |
| *C12Q 1/68* | (2006.01) |
| *C23Q 1/37* | (2006.01) |
| *C07H 21/04* | (2006.01) |
| *A01N 25/00* | (2006.01) |

(52) U.S. Cl. ............ 435/212; 435/183; 435/4; 435/6; 435/24; 514/789; 536/23.2; 536/23.7; 536/23.5

(58) Field of Classification Search ............. 435/189, 435/183, 6, 212, 440, 4, 18, 24, 69.1; 530/350; 536/24.5, 23.2, 23.7; 514/789
See application file for complete search history.

(56) References Cited

U.S. PATENT DOCUMENTS 5,976,796 A * 11/1999 Szalay et al. ............ 435/6

(Continued)

FOREIGN PATENT DOCUMENTS

EP   1 130 029   9/2001

(Continued)

OTHER PUBLICATIONS

Reiss et al. Specificity of binding of NH2-terminal residue of proteins to ubiquitin-protein ligase. Use of amino acid derivatives characterize specific binding sites. J Biol Chem. Feb. 25, 1988;263(6):2693-8.*

(Continued)

*Primary Examiner*—P. Achutamurthy
*Assistant Examiner*—Yong D. Pak
(74) *Attorney, Agent, or Firm*—DLA Piper US LLP

(57) ABSTRACT

The present invention is based on the discovery that a polypeptide containing the JAB subunit or the JAM domain has peptidase activity, e.g., isopeptidase activity. The present invention provides polypeptides and crystalline polypeptides containing the JAM domain and methods of using such polypeptides to screen for agents capable of affecting the peptidase activity of the polypeptides. The present invention also provides methods of using the JAM domain for rational drug design or identifying agents capable of affecting the peptidase activity of the JAM domain.

24 Claims, 4 Drawing Sheets

U.S. PATENT DOCUMENTS 6,165,731 A 12/2000 Deshaies et al.

FOREIGN PATENT DOCUMENTS

| JP | WO00/29436 | 5/2000 |
| WO | WO00/79267 | 12/2000 |

OTHER PUBLICATIONS

Deshaies et al. SCF and Cullin/Ring H2-based ubiquitin ligases. Annu Rev Cell Dev Biol. 1999;15;435-67.*

Bech-Otschir, et al., "COP9 Signalsome-specific Phosphorylation Target p53 to Degradation by the Ubiquitin System", *The EMBO J.* 20(7):1630-1639, (2001).

Ciechanover, et al., "Ubiquitin-mediated Proteolysis: Biological Regulation Via Destruction", *BioEssays* 22:442-451, (2000).

Eytan, et al., "Ubiquitin C-terminal Hydrolase Activity Associated with the 26 S Protease Complex", *J. of Bio. Chem.* 268(7):4668-4674, (Mar. 1993).

Löwe, et al., "Crystal Structure of the 20S Proteasome from the Archaeon *T. acidophilum* at 3.4 Resolution", *Sci.*, 268:533-539, (Apr. 1995).

Lyapina, et al., "Promotion of NEDD8-CUL1 Conjugate Cleaveage by COP9 Signalsome", *Sci.* 292:1382-1385, (May 2001).

Tomoda, et al., "Degradation of the Cyclin-dependent-kinase Inhibitor p27$^{kip1}$ is instigated by Jab1", *Nat.* 398:160-165, (Mar. 1999).

Wei, et al., "The COP9 Complex is Conserved Between Plants and Mammals and is Related to the 26S Proteasome Regulatory Comples", *Cur. Bio.* 8(16):919-922, (1998).

Chamovitz and Segal, "JAB1/CSN5 and the COP9 Signalsome: A Complex Situation," *EMBO Reports*, vol. 2, No. 2, 2001, pp. 96-101.

Ciechanover, Aaron et al., "Ubiquitin-Mediated Proteolysis: Biological Regulation Via Destruction," *BioEssays*, vol. 22, 2000, pp. 442-451.

Glickman, Michael H. et al., "The Regulatory Particle of the *Saccharomyces cerevisiae* Proteasome," *Molecular and Cellular Biology*, vol. 18, No. 6, Jun. 1998, pp. 3149-3162.

Groll, Michael et al., "The Eukaryotic 20S Proteaome: A Potential Target for Drug Development," In DFG-Schwerpunkt, Strktur, Funktion and Regulation des 20S/26S Ubiquitin-Proteasomesystems Kolloquium, May 23-25, 2001, Program Abstract, accessed on Internet Jun. 20, 2002 at www.dfg-sp-ubiquitin.de.

Lyapina, Svetlana et al., "Promotion of NEDD8-CUL1 Conjugate Cleavage By CPO9 Signalosome," *Science*, vol. 292, May 18, 2001, pp. 1382-1385.

Meiners, Silke et al., "Role of the Ubiquitin-Protease Pathway In Vascular Restenosis-Proteasome Inhibition As A New Therapeutic Approach," In DFG-Schwerpunkt, Strktur, Funktion and Regulation des 20S/26S Ubiquitin-Proteasomesystems Kolloquium, May 23-25, 2001, Program Abstract, accessed on Internet Jun. 20, 2002 at www.dfg-sp-ubiquitin.de.

Wei, Ning et al., "The COP9 Complex Is Conserved Between Plants and Mammals and Is Related to the 26S Proteasome Regulatory Complex," *Current Biology*, vol. 8, No. 16, Jul. 27, 1998, pp. 919-922 and S1 and S2.

* cited by examiner

```
AMSH1    THNEFTITHVIVP--KQSAGPDYCDMENVEELFNVQDQHD---LLTLGWIETFPTQTAFLS
AMSH2    THNEFTITHVIVP--KQSAGPDYCDMENVEELFNVQDQHD---LLTLGWIETFPTQTAFLS
AMSH     MRNEFTITHVLIP--KQSAGSDYCNTENEEELFLIQDQQG---LITLGWIETFPTQTAFLS
Rpn11    TVRVIDVFAMFQS--GTGVSVEAVDPVFQAKMLDMLKQTGRPEMVVGWYHSEPGFGCWLS
Jab1     TMIIMDSFALPVEGTETRVNAQAAAYEYMAAYIENAKQVGRIENAIGWYHSEPGYGCWLS
                :    :       ..  :         :   .*  .    .:** ##*   .:**

AMSH1    SVELHTHCSYQLMLPEAIAIVCSPKHKDTG-----IFRLTNAGMLEVSACKKKGFH--PH
AMSH2    SVELHTHCSYQLMLPEAIAIVCSPKHKDTG-----IFRLTNAGMLEVSACKKKGFH--PH
AMSH     SVELHTHCSYQMMLPESVAIVCSPKFQETG-----FFKLTDHGLEEISSCRQKGFH--PH
Rpn11    GVEINTQQSFEALSERAVAVVVDPIQSVKGKVVIDAFRLINAHMMVLGHEFRQTTSNLGH
Jab1     GIEVSTQMLNQQFQEPFVAVVIDPTRTISAG----KVNLGAFRTYPKGYKPPDEGPSEYQ
         .:#::  :     :  :  :*::  .*       ..:*       >   .        :

AMSH1    TKEPRLFSICKHV--LVKDIKI----------IVLDLR----------------------
AMSH2    TKEPRLFSIQKFLSGIISGTAL----------EHEPLKIGYGPNGFPLLGISRSSSPSEQ
AMSH     SKDPPLFCSCSHVT--VVDRAV----------TITDLR----------------------
Rpn11    LNKPSIQALIHGLNRHYYSITINYRKNELEQKMLLNLHKKSWMEGLTLQDYSEHCKHNES
Jab1     TIPLNKIEDFGVHCKQYYALEVSYFKSSLDRKLLELLWNKYWVNTLSSSSLLTNADYTTG
                                       :            :   *

AMSH1    -----------------------------------------------------------
AMSH2    L----------------------------------------------------------
AMSH     -----------------------------------------------------------
Rpn11    VVKEMLELAKNYNKAVEEEDKMTPEQLAIKNVGKQDPKRHLEEHVDVLMTSNIVQCLAAM
Jab1     QVFDLSEKLEQSEAQLGRGSFMLG--LETHDRKSEDKLAKATRDSCKTTIEAIHGLMSQV

AMSH1    ----------
AMSH2    ----------
AMSH     ----------
Rpn11    LDTVVFK----
Jab1     IKDKLFNQINIS
```

FIGURE 1

```
AMSH1    ---------------MFDHIDVSLSEERVRALSKLGCNITISEDITPRR  35
AMSH2    MDQPFTVNSLKKLAAMPDHTDVSLSFEERVRALSKLGCNITISEDITPRR  50
AMSH     -------------MSDRGDVSLPPEDRVRALSQLGSAVEVNEDIPPRR    35
                        *.**  ****.**.*****,** .  . ..***.***

AMSH1    YFRSGVEMERMASVYLEEGNLENAFVLYNKFITLFVEKLPNHRDYQQCAV  85
AMSH2    YFRSGVEMERMASVYLEEGNLENAFVLYNKFITLFVEKLPNHRDYQQCAV  100
AMSH     YFRSGVEIIRMASIYSEEGNIEHAFILYNEYITLFIEKLPKHRDYKSAVI  85
         *******. ****.* ****.*.**.*****.****.****.****....

AMSH1    PEKQDIMKKLKEIAFPRTDELKNDLLKKYNVEYQEYLQSKNKYKAEILKK  135
AMSH2    PEKQDIMKKLKEIAFPRTDELKNDLLKKYNVEYQEYLQSKNKYKAEILKK  150
AMSH     PEKKDTVKKLKEIAFPKAEEIKAELIERYTKEYTEYNEEKKKEAEELARN  135
         ***.*  .******.*..***  .*** .* ,**  **  ,.*.*    *. **

AMSH1    LEHQRLIEAERKRIAQMRQQQLESEQFLFFEDQLKKQELARGQMRSQQTS  185
AMSH2    LEHQRLIEAERKRIAQMRQQQLESEQFLFFEDQLKKQELARGQMRSQQTS  200
AMSH     MAIQQELEKEKQRVAQQKQQQLEQEQFHAFEEMIRNQELEKERLKIVQEF  185
         .  * .* *..*.** *****.***  **. ..**. . ...   *

AMSH1    G-LSEQIDGSALSCFS--THQNNSLLNVFADQPNKSDATNYASHSPPVNR  232
AMSH2    G-LSEQIDGSALSCFS--THQNNSLLNVFADQPNKSDATNYASHSPPVNR  247
AMSH     GKVDPGIGGPLVPDLEKPSLDVFPTLIVSSIQPSDCHTTVRPAKPPVVDR  235
         * ..  ..*..  .*.  *.  .  .    *,*  .*.....*   ..*.*  *.*

AMSH1    ALTPAATLSAVQNLVVEGLRCVVLPEDLCHKFLQLAESNTVRGIETCGIL  282
AMSH2    ALTPAATLSAVQNLVVEGLRCVVLPEDLCHKFLQLAESNTVRGIETCGIL  297
AMSH     SLKPGALSNSESIPTIDGLRHVVPGRLCPQFLQLASANTARGVETCGIL  285
         .*.*.*  .*. .  . .**.** .* ** .****.*.**.**.*****

AMSH1    CGKLTHNEFTITHVIVPKQSAGPDYCDMENVEELFNVQDQHDLLTLGWI  332
AMSH2    CGKLTHNEFTITHVIVPKQSAGPDYCDMENVEELFNVQDQHDLLTLGWI  347
AMSH     CGKLMRNEFTITHVLIPKQSAGSDYCHTENEEELFLIQDQQGLITLGWI  335
         **** .********..*****.***.  ***.* *** .**.  *.****

AMSH1    TPTQTAFLSSVLHTHCSYQLMLPEAIAIVCSPKHRDTGIFRLTNAGML  382
AMSH2    TPTQTAFLSSVLHTHCSYQLMLPEAIAIVCSPKHRDTGIFRLTNAGML  397
AMSH     TPTQTAFLSSVLHTHCSYQMMLPESVAIVCSPKFQETGFFKLTDEGLE  385
         .********** ******** ***  .********    **.*  **. .  **  .*.*.

AMSH1    EVSACKKKGFHPHTKEPRLFSICKHV--LVKDIKIIVLDLR---------  421
AMSH2    EVSACKKKGFHPHTKEPRLFSIQKFLSGIISGTALKMEPLKIGYGPNGFP  447
AMSH     EISSCRQKGFHPHSKDPPLFCSCSHVT--VVDRAVTITDLR---------  424
         *.*.*..*****..*.*.**.. . *  ..*.   .* .  *

AMSH1    ---------------
AMSH2    LLGISRSSSPSEQL  461
AMSH     ---------------
```

FIGURE 2

```
COP9_su5_Hs    VGRLENAIGWYHSHPGYGCWLSGIDVSTQMLNQQFQEPFVA--VVIDPTRTISAGKVNLG
COP9_su5_Dm    VGRMEHAVGWYHSHPGYGCWLSGINVSTQMLNQTYQEPFVA--IVVDPVRTVSAGKVCLG
COP9_su5_At    AGRLENVVGWYHSHPGYGCWLSGIDVSTQRLNQQHQEPFLA--VVIDPTRTVSAGKVEIG
COP9_su5_Ce    EGRKEKVVGWYHSHPGYGCWLSGIDVSTQTLNQKFQEPWVA--IVIDPLRTMSAGKVDIG
AF2198_Arcfu   LPIGMKVFGTVHSHPSPSCRPSEEDLSLFTRFGKYHIIVCY--PYDENSWKCYNRKGEEV
PH0451_Pyrho   MPHDESIKGTFHSHPSPFPYPSEGDLMFFSKFGGIHIIAAF--PYDEDSVKAFDSEGREV
TVN1035_Thevo  KPIDFSLVGSVHSHPSGITKPSDEDLRMFSLTGKIHIIVGY--PYNLKDYSAYDRSGNKV
MTH971_Metth   LPPFTGAVGSVHSHPGPVNLPSAADLHFFSKNGLFHLIIAH--PYTMETVAAYTRNGDPV
aq_1691_Aquae  ISKGMEIVGVYHSHPDHPDRPSQFDLQRAFPDLSYIIFSVQ--KGKVASYRSWELKGDKF
RV1334_Myctu   EDADEVPVVIYHSHTATEAYPSRTDVKLATEPDAHYVLVSTRDPHRHELRSYRIVDGAVT
RadC_Ecoli     IKINASALILAHNHPSGCAEPSKADKLITERIIKSCQFMDL--RVLDHIVIGRGEYVSFA
               '''''''''''''''''''''''''''HSHP'''''S  ''D
```

FIGURE 3

```
COP9_su5_Hs    VGRLENAIGWYHSHPGYGCWLSGIDVSTQMLNQQFQEPFVA--VVIDPTRTISAGKVNLG
COP9_su5_Dm    VGRMEHAVGWYHSHPGYGCWLSGINVSTQMLNQTYQEPFVA--IVVDPVRTVSAGKVCLG
COP9_su5_At    AGRLENVVGWYHSHPGYGCWLSGIDVSTQRLNQQHQEPFLA--VVIDPTRTVSAGKVEIG
COP9_su5_Ce    EGRKEKVVGWYHSHPGYGCWLSGIDVSTQTLNQKFQEPWVA--IVIDPLRTMSAGKVDIG
Pad1_Dm        TGRPEMVVGWYHSHPGFGCWLSGVDINTQQSFEALSERAVA--VVVDPIQSVKG-KVVID
Pad1_Hs        TGRPEMVVGWYHSHPGFGCWLSGVDINTQQSFEALSERAVA--VVVDPIQSVKG-KVVID
Sks1_Dd        TGRDEIVIGWYHSHPGFGCWLSSVDVNTQQSFEQLQSRAVA--VVVDPLQSVRG-KVVID
Pad1_Sc        TGRDQMVVGWYHSHPGFGCWLSSVDVNTQKSFEQLNSRAVA--VVVDPIQSVKG-KVVID
'''''''''''''''''''''''''''''''' HSHP''''''S 'D
```

REGULATION OF TARGET PROTEIN ACTIVITY THROUGH MODIFIER PROTEINS

CROSS REFERENCE TO RELATED APPLICATIONS

This application claims priority under 35 U.S.C. 119(e)(1) to U.S. Provisional Application No. 60/261,314, filed on Jan. 12, 2001, U.S. Provisional Application No. 60/322,322, filed on Sep. 14, 2001, and U.S. Provisional Application No. 60/322,030, filed on Sep. 14, 2001, all of which are incorporated herein by reference.

FIELD OF THE INVENTION

This invention relates generally to the field of peptidase activity, more specifically deconjugation, removal, or separation of a modifier protein from a target protein, e.g., de-neddylation or de-ubiquitination.

BACKGROUND OF THE INVENTION

The function of a protein is regulated via various means in a cell. One way to regulate protein function is via conjugation and deconjugation of a modifier protein to a target protein, e.g., neddylation and de-neddylation or ubiquitination and de-ubiquitination.

The major route for protein degradation in the nucleus and cytoplasm of eukaryotic cells is via the ubiquitin/26S proteasome pathway. The 26S proteasome comprises two major subparticles: the 20S proteasome and the 19S regulatory particle. The 20S proteasome is a cylindrical structure with an internal cavity that contains the peptidase active sites. Substrates of the proteasome are inserted into the cylinder, where they are susceptible to digestion by the peptidase active sites of the 20S proteasome. Entry into the 20S proteasome cylinder is governed by the 19S regulatory particle, which caps the ends of the 20S cylinder.

The 19S regulatory particle binds ubiquitinated substrates and translocates them into the inner cavity of the 20S cylinder, where they are degraded. The 19S regulatory particle can be further subdivided into two multiprotein complexes: the base and the lid. The base comprises a set of six ATPases that are thought to unfold substrates and translocate them into the 20S proteasome. The lid is comprised of a set of eight proteins of unknown function. Biochemical data indicate that the presence of the lid renders the proteasome selective for degrading ubiquitinated proteins, but the basis for this selectivity is not known.

The lid subcomplex of the 26S proteasome is evolutionarily related to the COP9-signalosome complex, but the significance of this similarity has remained unknown. There are reports in the literature that 26S proteasome preparations contain a variety of associated ubiquitin isopeptidase activities (Eytan, E., et al., J. Biol Chem. 268:4668-74 (1993); Verma, et al., Mol Biol Cell 11:3425 (2000)). However, none of these reports demonstrate that an ubiquitinated substrate can be completely deubiquitinated by purified 26S proteasome to yield unmodified substrate. The failure to detect such a reaction product may be due to a tight coupling between the deubiquitination of a substrate and its subsequent degradation within the internal cavity of the 20S proteasome.

Proteins that are destined for degradation by the ubiquitin/26S pathway are marked by the attachment of a multiubiquitin chain to the side chains of lysine residues on the target protein. The ubiquitinated protein is then recognized by the 26S proteasome by a mechanism that remains poorly understood. Subsequently the ubiquitinated protein is disengaged from any tightly bound partners, unfolded, and translocated into the central cavity of the 20S complex, where it is exhaustively degraded by the proteolytic active sites that are present in this inner cavity.

Despite many years of intensive study of this system, it remains unclear what happens to the substrate-bound multiubiquitin chains that target the substrate for degradation. It appears that ubiquitin is not degraded by the proteasome and in fact is recycled. However it remains unclear if the ubiquitin chains enter the inner cavity of the proteasome and emerge unscathed, or are cleaved from the substrate protein prior to or during its translocation into the inner cavity of the 20S. In prior work (Eytan, E., et al., J. Biol Chem. 268:4668-74 (1993)), it was demonstrated that there is an isopeptidase activity or activities associated with the intact 26S proteasome that is able to release free ubiquitin monomers from ubiquitinated substrates that are degraded by the 26S proteasome. It was demonstrated that this activity is sensitive to the metal ion chelator 1,10-phenanthroline, but the identity of the polypeptides that harbors this activity was not established, nor was it established that this activity is intrinsic to the 26S proteasome as opposed to being intrinsic to a protein that binds transiently to the 26S proteasome. This prior work also fails to disclose that the ubiquitin isopeptidase activity is critical to the protein-degrading function of the 26S proteasome.

Nedd8 is an ubiquitin-like protein. Like ubiquitin, it is covalently linked via its carboxy terminus to the side-chain amino group of lysine residues in target proteins (referred to as neddylation). The attachment of Nedd8 to target proteins requires the combined action of Nedd8-activating enzyme composed of Ula1 and Uba3 subunits (analogous to ubiquitin-activating enzyme, E1), and Ubc12, which is homologous to the ubiquitin-conjugating enzymes (E2s). There is no known requirement for an activity equivalent to the ubiquitin ligase (E3) component of ubiquitination pathways. The Nedd8 modification, like ubiquitination, is probably dynamic. However little is known about the nature of the enzymes that would cleave Nedd8 from its targets (i.e. deneddylate, also referred to as 'deneddylation' or 'denedydylating' activity).

A ubiquitin isopeptidase (USP21) has been shown to be able to deneddylate Cul1-Nedd8 conjugates, and a second enzyme UCH-L3, has been shown to be able to cleave Nedd8-containing fusion proteins at the C-terminus of Nedd8 to release mature Nedd8 (Nedd8, like ubiquitin, is made as a precursor with additional C-terminal residues that must be removed before it can be conjugated to proteins). Despite the fact that both USP21 and UCH-L3 can metabolize Nedd8-based substrates, they also work on ubiquitin-based substrates, and it remains unclear whether their biochemical activity towards Nedd8 is relevant in the context of a cell.

In contrast to ubiquitin, the attachment of Nedd8 to proteins does not mark them for degradation. Rather, it appears as if neddylation acts to modify protein function, much like phosphorylation. The only proteins that have been found to be conjugated with Nedd8 to date are the cullins. The cullins are a family of six related proteins that bind a RING-H2 domain protein to form the catalytic core of multisubunit ubiquitin ligases. All cullins examined have been shown to be modified by attachment of Nedd8, and neddylation of Cul1 has been shown to potentiate the ubiquitin ligase of the SCF complex within which Cul1 resides. Thus, for Cul1-based ubiquitin ligases, neddylation serves as a positive regulator of activity. However, for other cullin-based ubiquitin ligases, the impact of neddylation remains uncertain.

The COP9/signalosome (hereafter referred to as CSN) was originally identified as a regulator of photomorphogenetic development in plants. In seedlings grown in the dark, CSN enables a putative ubiquitin ligase known as COP1 to mediate rapid turnover of the transcriptional regulatory protein HY5 in the nucleus. In seedlings that have been exposed to light or in CSN mutants, COP1 redistributes from the nucleus to the cytoplasm, thereby stabilizing HY5 and allowing it to accumulate in the nucleus. HY5, in turn, activates the transcription of a broad palette of genes that mediate photomorphogenetic development. Although the general physiological role of CSN in photomorphogenesis has been defined, little is known about other potential physiological functions for CSN, and the biochemical function of CSN remains completely elusive. It has been suggested that CSN might play a role in ubiquitin-dependent proteolysis, based on the observation that the eight subunits of CSN share homology to subunits of the lid subcomplex of the 19S regulator of the 26S proteasome. However, a similar pattern of homology is shared with subunits of the eukaryotic initiation factor-3 (eIF3) complex. Besides plants, CSN complexes have been discovered in human cells, *Drosophila*, and the fission yeast *Schizosaccharomyces pombe*. Surprisingly, the budding yeast *Saccharomyces cerevisiae* does not contain an apparent CSN complex, but does contain a gene homologous to the CSN5/JAB 1 subunit of CSN complex, thereby implicating CSN5 as being the critical component of CSN.

There is a need in the art to identify the active domain and site of peptidase activity, e.g., isopeptidase activity of a protein involved in deconjugation of a modifier protein from a target protein, e.g., de-neddylation or de-ubiquitination and use such active site for drug design. There is also a need in the art to provide screening methods for agents capable of affecting the peptidase activity, e.g., isopeptidase activity of a protein and use such agents to treat relevant conditions.

SUMMARY OF THE INVENTION

The present invention is based on the discovery that the JAB subunit, more specifically the JAM domain is responsible for the peptidase activity of a protein, e.g., the protein's ability of cleaving a peptide bond between the carboxy terminus of a modifier protein and a free amino group of a target protein. The present invention provides polypeptides and crystalline polypeptides containing the JAM domain and methods of using such domain to treat conditions associated with peptidase activity, especially isopeptidase activity and methods to screen for agents that are capable of modulating its peptidase activity. The present invention also provides methods of using such domain to identify or design compounds that are candidates for modulators of the peptidase activity.

In one embodiment, the present invention provides an isolated polypeptide containing a JAM domain consisting essentially of an amino acid sequence of HXHXXXXXXXXXXD (SEQ ID NO. 1), wherein H is histidine, D is aspartate, and X is any amino acid and wherein the JAM domain is not adjacent to an amino acid sequence that is naturally adjacent to the domain.

In another embodiment, the present invention provides an isolated crystalline polypeptide containing a JAM domain consisting essentially of an amino acid sequence of HXHXXXXXXXXXXD, wherein H is histidine, D is aspartate, and X is any amino acid.

In yet another embodiment, the present invention provides an isolated monoclonal antibody that specifically binds to an epitope within a JAM domain of a polypeptide, wherein the JAM domain consists essentially of an amino acid sequence of HXHXXXXXXXXXXD, wherein H is histidine, D is aspartate, and X is any amino acid.

In still another embodiment, the present invention provides a method of identifying an inhibitor of a polypeptide by rational drug design. The polypeptide comprises a JAM domain consisting essentially of an amino acid sequence of HXHXXXXXXXXXXD, wherein H is histidine, D is aspartate, and X is any amino acid. The method comprises designing a potential inhibitor for the polypeptide that will form a bond with the JAM domain based upon the crystal structure co-ordinates of the polypeptide, synthesizing the inhibitor, and determining whether the potential inhibitor inhibits the activity of the polypeptide.

In another embodiment, the present invention provides a method of deconjugating a modifier protein from a target protein. The modifier protein is conjugated to the target protein via a peptide bond between the carboxy terminus of the modifier protein and a free amino group of the target protein. The method comprises contacting the target protein to a polypeptide comprising a JAM domain consisting essentially of an amino acid sequence of HXHXXXXXXXXXXD, wherein H is histidine, D is aspartate, and X is any amino acid.

In another embodiment, the present invention provides a method of screening for an agent that affects deconjugation of a modifier protein from a target protein. The modifier protein is conjugated to the target protein via a peptide bond between the carboxy terminus of the modifier protein and a free amino group of the target protein. The method comprises incubating in the presence and absence of a test agent, the target protein and a polypeptide comprising a JAM domain consisting essentially of an amino acid sequence of HXHXXXXXXXXXXD, wherein H is histidine, D is aspartate, and X is any amino acid and determining the effect of the test agent. An increase or decrease in the amount of the target protein not conjugated to the modifier protein caused by the test agent is indicative of an agent affecting deconjugation of the modifier protein from the target protein.

In another embodiment, the present invention provides an agent identified by the method of the present invention.

In another embodiment, the present invention provides a method of increasing conjugation of a modifier protein to a target protein. The modifier protein is conjugated to the target protein via a peptide bond between the carboxy terminus of the modifier protein and a free amino group of the target protein in a cell comprising inhibiting the activity of a polypeptide comprising a JAM domain consisting essentially of an amino acid sequence of HXHXXXXXXXXXXD, wherein H is histidine, D is aspartate, and X is any amino acid, thereby increasing the conjugation of the modifier protein to the target protein.

In still another embodiment, the present invention provides a method of treating a condition of neoplastic growth, angiogenesis, infection, chronic inflammation, asthma, ischemia and reperfusion injury, multiple sclerosis, rheumatoid arthritis, or psoriasis. The method comprises administering an agent identified by the method of the present invention to a subject in need of such treatment.

SUMMARY OF THE FIGURES

FIG. 1 shows the sequence alignment of human AMSH proteins (AMSH 1, is amino acid residue 281-421 of SEQ ID NO:5; AMSH2, is amino acid residues 302-461 of SEQ ID NO: 6; AMSH, SEQ ID NO: 7) with human JAB1 (SEQ ID NO:3) and Rpn11 (SEQ ID NO:4). Conserved active site residues are boxed.

FIG. 2 shows the sequence alignment of AMSH (SEQ ID NO:7), AMSH1 is amino acid residue 281-421 of SEQ ID NO:5, and AMSH2 is amino acid residues 302-461 of SEQ ID NO: 6. The critical conserved active site residues are boxed.

FIG. 3 shows that sequence alignment of COP9 subunit 5 (COP9su5 Hs, SEQ ID NO:8; COP9 su5 Dm, SEQ ID NO:9; COP9 su5 At, SEQ ID NO: 10; COP9 su5 Ce, SEQ ID NO:11) and orthologs (AF2198 ArcFu, SEQ ID NO: 12; PH0451 Pyrho, SEQ ID NO:13; TVN1035 Thevo, SEQ ID NO:14; MTH971 Metth, SEQ ID NO:15; aq 1691 Aquae, SEQ ID NO:16; RV1334 Myctu, SEQ ID NO:17; and RadC Ecoli, SEQ ID NO:18) from different eukaryotic species reveals conserved histidine, serine, and aspartate residues that are also found in a set of prokaryotic and archaebacterial proteins.

FIG. 4 shows the alignment of Rpn11 orthologs (Pad 1 Dm, SEQ ID NO:19; Pad1Hs, SEQ ID NO:20; and Sks1 Dd, SEQ ID NO:21; and Pad1 Sc, SEQ ID NO:22) and CSN5/JAB 1 orthologs from different species (COP9 su5 Hs, SEQ ID NO:8; COP9 su5 Dm, SEQ ID NO:9; COP9 su5 At, SEQ ID NO:10; and COP9 su5 Ce, SEQ ID NO:11).

DESCRIPTION OF THE PREFERRED EMBODIMENTS

The present invention relates in general to active sites responsible for the peptidase activity, e.g., isopeptidase activity of a protein. It is a discovery of the present invention that a polypeptide containing the JAB subunit, more specifically the JAM domain has peptidase activity, e.g., cleavage of a peptide bond between the carboxy terminus of a modifier protein and a free amino group of a target protein. Polypeptides containing the JAB subunit, more specifically the JAM domain can be used to treat conditions associated with the peptidase activity, screen for agents capable of modulating the peptidase activity, and identify or design compounds that are candidates for modulators of the peptidase activity.

According to the present invention, a modifier protein can be deconjugated, removed, or separated from a target protein by exposing or contacting the target protein to a polypeptide containing a subunit characterized as JAB subunit or a domain characterized as JAM domain. The modifier protein is usually associated with a target protein via a peptide bond between the carboxy terminus of the modifier protein and a free amino group of the target protein. A free amino group generally includes, without limitation, an amino group of the amino terminus of a polypeptide or the epsilon amino group of lysine residues of a polypeptide.

According to the present invention, the JAB subunit may be the JAB1 subunit of COP9/signalsome (CSN) as disclosed in FIG. 1 (SEQ ID NO. 3) or the Rpn11 subunit of 26S proteasome as disclosed in FIG. 1 (SEQ ID NO. 4). A polypeptide subunit can be characterized as JAB subunit if it has the sequence characteristics of the JAB1 or Rpn11 subunit. Normally a polypeptide subunit is deemed to have the sequence characteristics of the JAB1 or Rpn11 subunit if it contains the JAM domain or is a homolog or ortholog of JAB1 or Rpn11 subunit. For example, FIG. 3 shows various orthologs of JAB1 from different species while FIG. 4 shows various orthologs of Rpn11 and JAB1 including an alignment of orthologs of Rpn11 and JAB1 from different species.

Polypeptides containing a subunit characterized as JAB subunit can be any known or to be discovered polypeptides, proteins, or complexes thereof. For example, the polypeptides may be a polypeptide complex of CSN containing JAB1 subunit, 26S proteasome containing Rpn11, AMSH, AMSH1, AMSH2, or C6-1A. CSN has previously been identified as a regulator of photomorphogenetic development in plants. 26 proteasome is involved in various activities, e.g., ubiquitin/26S proteasome pathway while AMSH, AMSH1, and AMSH2 are involved in cytokine signaling, TGF-β signaling, and survival of hippocampal neurons. C6-1A has been observed to be fused to the T cell receptor alpha chain gene by a chromosomal translocation in a patient with T-cell leukemia.

According to one embodiment of the invention, the deconjugation, removal, or separation of a modifier protein from a target protein is achieved by exposing or contacting the target protein to a polypeptide containing a domain characterized as the JAM domain. The JAM domain of the present invention includes any domain containing the amino acid sequence of HXHXXXXXXXXXXD (SEQ ID NO. 1), with H being histidine, D being aspartate, and X being any amino acid. In one embodiment, the JAM domain is any domain having an amino acid sequence of GW(Y/I)H(S/T)HPXXXXXXSXXD (SEQ ID NO. 2), with G being glycine, W being tryptophan, Y being tyrosine, I being isoleucine, H being histidine, P being proline, S being serine, T being threonine, D being aspartate, X being any amino acid, Y/I being either Y or I, and S/T being either S or T.

In another embodiment, the JAM domain is from a human protein and has the amino acid sequence of SEQ ID NO. 2. In yet another embodiment, the JAM domain includes any domain having the same peptidase activity, e.g., isopeptidase activity of a domain containing the amino acid sequence of SEQ ID NO. 1 or SEQ ID NO. 2. In still another embodiment, the JAM domain contains a metalloenzyme, e.g., metalloprotease active site and provides peptidase activity, e.g., isopeptidase activity.

One feature of the present invention provides isolated polypeptides containing a domain characterized as the JAM domain. For example, the present invention provides an isolated polypeptide containing the JAM domain which is not surrounded by or adjacent to any amino acid sequences that are naturally adjacent to such JAM domain.

Another feature of the present invention provides isolated crystalline polypeptides containing the JAM domain. The crystalline polypeptides can be made by any suitable means known to one skilled in the art. For example, polypeptides containing the JAM domain can be crystallized by equilibrating saturated solutions of the polypeptides with salts, volatile organic compounds, and other organic compounds at various controlled temperatures.

Yet another feature of the present invention provides isolated monoclonal antibodies that specifically bind to an epitope within the JAM domain. Such monoclonal antibodies can be prepared by any means known to one skilled in the art. For example, whole or partial amino acid sequences of the JAM domain can be used as an antigen to obtain monoclonal antibodies. In one embodiment, the amino acid sequence used as antigen contains the histidine or aspartate in SEQ ID NO. 1 or SEQ ID NO. 2.

Polypeptides containing the JAM domain include all known or to be discovered polypeptides, proteins, or complexes thereof. For example, Table 1 shows various polypeptides, proteins, or fragments thereof from different species that contain the JAM domain.

TABLE 1

JAM-Domain-Containing Proteins From Model Organisms*

Bacteria

Most bacteria encode one and some 2-4 paralogs of the DNA repair protein
RadC, which is a distinct version of the JAM domain.
In addition:
*Aquifex aeolicus* [aquificales] taxid 63363
gi|15606783|ref|NP_214163.1| (NC_000918) hypothetical prot . . .
*Mycobacterium tuberculosis* H37Rv [high GC Gram+] taxid 83332
gi|15608474|ref|NP_215850.1| (NC_000962) hypothetical prot . . .
Synechocystis sp. PCC 6803 [cyanobacteria] taxid 1148
gi|16330214|ref|NP_440942.1| (NC_000911) unknown protein [ . . .
*Deinococcus radiodurans* [eubacteria] taxid 1299
gi|15805429|ref|NP_294125.1| (NC_001263) conserved hypothe . . .
*Pseudomonas aeruginosa* [g-proteobacteria] taxid 287
gi|15595836|ref|NP_249330.1| (NC_002516) conserved hypothe . . .
gi|15597298|ref|NP_250792.1| (NC_002516) hypothetical prot . . .
*Coxiella burnetii* [g-proteobacteria] taxid 777
gi|10956045|ref|NP_052867.1| (NC_002131) hypothetical prot . . .
gi|1070034|emb|CAA63684.1| (X93204) orf 112 [Coxiella burn . . .
gi|10956011|ref|NP_052361.1| (NC_002118) orf 169; similari . . .
Archaea

*Pyrococcus abyssi* [euryarchaeotes] taxid 29292
gi|14520886|ref|NP_126361.1| (NC_000868) hypothetical prot . . .
gi|14521781|ref|NP_127257.1| (NC_000868) hypothetical prot . . .
*Methanothermobacter thermautotrophicus* [euryarchaeotes] taxid 145262
gi|15678989|ref|NP_276106.1| (NC_000916) unknown [Methanot . . .
Halobacterium sp. NRC-1 [euryarchaeotes] taxid 64091
gi|16554503|ref|NP_444227.1| (NC_002607) Uncharacterized c . . .
gi|15789943|ref|NP_279767.1| (NC_002607) Vng0778c [Halobac . . .
*Archaeoglobus fulgidus* [euryarchaeotes] taxid 2234
gi|11499780|ref|NP_071023.1| (NC_000917) conserved hypothe . . .
*Aeropyrum pernix* [crenarchaeotes] taxid 56636
gi|14600889|ref|NP_147414.1| (NC_000854) hypothetical prot . . .
*Sulfolobus solfataricus* [crenarchaeotes] taxid 2287
gi|15897071|ref|NP_341676.1| (NC_002754) Hypothetical prot . . .
Eukaryotes

*Saccharomyces cerevisiae* (baker's yeast) [fungi] taxid 4932
gi|14318526|ref|NP_116659.1| (NC_001138) Suppressor of mut . . .     Rpn11p
gi|6319985|ref|NP_010065.1| (NC_001136) Hypothetical ORF; . . .     Rri1p
*Schizosaccharomyces pombe* (fission yeast) [fungi] taxid 4896
gi|3334476|sp|P41878|PAD1_SCHPO PROTEIN PAD1/SKS1 > gi|7493 . . .
gi|11281515|pir||T44427 hypothetical protein-fission yea . . .
gi|7492119|pir||T37756 jun activation domain binding prote . . .
gi|9588467|emb|CAC00558.1| (AL390814) similarity to human . . .
*Arabidopsis thaliana* (thale cress) [eudicots] taxid 3702
gi|15224003|ref|NP_177279.1| (NC_003070) c-Jun coactivator . . .
gi|15219970|ref|NP_173705.1| (NC_003070) putative JUN kina . . .
gi|15237785|ref|NP_197745.1| (NC_003076) 26S proteasome, n . . .
gi|15229710|ref|NP_187736.1| (NC_003074) 26S proteasome re . . .
gi|15239230|ref|NP_196197.1| (NC_003076) 26S proteasome re . . .
gi|15218589|ref|NP_172530.1| (NC_003070) hypothetical prot . . .
gi|15221964|ref|NP_175311.1| (NC_003070) hypothetical prot . . .
gi|15231308|ref|NP_187338.1| (NC_003074) unknown protein [ . . .
gi|5902365|gb|AAD55467.1|AC009322_7 (AC009322) Putative sp . . .
gi|5091556|gb|AAD39585.1|AC007067_25 (AC007067) T10O24.25 . . .
gi|6573732|gb|AAF17652.1|AC009398_1 (AC009398) F20B24.2 [A . . .
gi|15220090|ref|NP_178138.1| (NC_003070) hypothetical prot . . .
gi|5902374|gb|AAD55476.1|AC009322_16 (AC009322) Hypothetic . . .
*Drosophila melanogaster* (fruit fly) [flies] taxid 7227
gi|17137694|ref|NP_477442.1| (NM_058094)CSN5-P1; Drosophi . . .
gi|4732109|gb|AAD28608.1|AF129083_1 (AF129083) COP9 signal . . .
gi|6434964|gb|AAF08394.1|AF145313_1 (AF145313) 26S proteas . . .
gi|7291779|gb|AAF47199.1| (AE003464) Mov34 gene product [D . . .
gi|7301945|gb|AAF57051.1| (AE003774) CG2224 gene product [ . . .
gi|7303518|gb|AAF58573.1| (AE003823) CG8877 gene product [ . . .
gi|7297828|gb|AAF53077.1| (AE003631) CG4751 gene product [ . . .
gi|6752672|gb|AAF27818.1|AF195189_1 (AF195189) yippee inte . . .
*Caenorhabditis elegans* [nematodes] taxid 6239
gi|17538322|ref|NP_500841.1| (NM_068440) B0547.1.p [Caenor . . .
gi|17553290|ref|NP_498470.1| (NM_066069) F37A4.5.p [Caenor . . .
gi|17535703|ref|NP_494712.1| (NM_062311) K07D4.3.p [Caenor . . .
gi|17508685|ref|NP_491319.1| (NM_058918) R12E2.3.p [Caenor . . .
*Homo sapiens* (human) [mammals] taxid 9606
gi|12734403|ref|XP_011713.1| (XM_011713) COP9 (constitutiv . . .
gi|5031981|ref|NP_005796.1| (NM_005805) 26S proteasome-ass . . .

TABLE 1-continued

JAM-Domain-Containing Proteins From Model Organisms* gi|7243127|dbj|BAA92611.1| (AB037794) KIAA1373 protein [Ho . . .
gi|5453545|ref|NP_006454.1| (NM_006463) associated molecul . . .
gi|16158201|ref|XP_055481.1| (XM_055481) KIAA1915 protein . . .
gi|1168719|sp|P46736|C61A_HUMAN C6.1A PROTEIN > gi|2135176| . . .
gi|4581082|gb|AAD24592.1|AC007292_2 (AC007292) R31167_1, p . . .
gi|7717235|gb|AAB30469.2| (S72931) T-cell receptor alpha c . . .
gi|14249610|ref|NP_116257.1| (NM_032868) hypothetical prot . . .

*Each protein is disclosed by accession numbers used in the protein and nucleic acid sequence databases (GenBank) maintained by the National Center for Biotechnology Information (NCBI; http://www.ncbi.nlm.nih.gov).

According to the present invention, a polypeptide containing the JAB subunit or JAM domain can additionally include any other amino acid sequences. In one embodiment, a polypeptide containing the JAB subunit or JAM domain has other amino acid sequences that do not interfere or inhibit the peptidase activity of the JAB subunit or JAM domain. In another embodiment, a polypeptide containing the JAB subunit or JAM domain has other amino acid sequences that enhance or facilitate the peptidase activity of the JAB subunit or JAM domain.

In yet another embodiment, a polypeptide containing the JAB subunit or JAM domain has other amino acid sequences that are associated with or determine the specificity of the peptidase activity of the JAB subunit or JAM domain. In still another embodiment, a polypeptide containing the JAB subunit or JAM domain has other amino acid sequences that inhibit or decrease the activity of the JAB subunit or JAM domain, and such inhibition can be released by a signal, e.g., second messenger, covalent modification, calcium or phosphorylation.

The modifier protein of the present invention can be any protein that modifies the activity or function of a target protein. In one embodiment, the modifier protein modifies a target protein through conjugation and deconjugation to the target protein, e.g., formation and cleavage of a peptide bond between the carboxy terminus of the modifier protein and a free amino group of the target protein. For example, APG12 and URM1 modifies a target protein via forming an isopeptide bond between the carboxy terminus of APG12 or URM1 and a free amino group of the target protein. A free amino group of a target protein usually includes, without limitation, an amino group of the amino terminus or epsilon amino group of lysine residues of the target protein.

One major class of modifier proteins is ubiquitin. Proteins destined for degradation may be marked by the attachment of a multiubiquitin chain to the side chains of lysine residues of the protein. Another class of modifier proteins include ubiquitin-like proteins, e.g., NEDD8, UBL1/SUMO, SMT3H2, SMT3H1, FAT10, Fau, UCRP/ISG15, or UBL5. In one embodiment, the modifier protein of the present invention includes any protein containing two glycine amino acids at its carboxy terminus after being processed.

The target protein of the present invention can be any protein whose activity or function is modified by a modifier protein. In one embodiment, a target protein is a protein which forms a peptide bond with a modifier protein, e.g., a peptide bond between the carboxy terminus of the modifier protein and a free amino group of the target protein. In another embodiment, a target protein is specific to a class of modifier proteins.

For example, the target protein of the present invention may be cullin proteins such as Cul1, Cul2, Cul3, Cul4A, Cul4B, and Cul5, which are known to be the target proteins of Nedd8. In one embodiment, the target protein of the present invention includes any protein having ubiquitin ligase activity or is part of a protein complex having ubiquitin ligase activity. In another embodiment, the target protein of the present invention includes any protein to which ubiquitin conjugates for processing or degradation, e.g., p53, IκB, NF-κB, β-adrenergic receptor, cyclin E, $p27^{Kip1}$, etc.

According to one embodiment of the present invention, the target protein used in the screening assays provided by the present invention can be any protein that produces a detectable signal upon deconjugation, removal, or separation from its modifier protein. Such detectable signal can be any assayable signal including, without limitation, enzymatic, spectroscopic, fluorescent, or functional signals, or a signal produced upon specific molecular interaction. For example, the target protein can be an enzyme such as peroxidase, alkaline phosphatase, and luciferase. The target protein can also be a fluorescent protein obtained via protein modification or a naturally fluorescent protein including, without limitation green fluorescent protein, yellow fluorescent protein, cyan fluorescent protein, dsRed, and the derivatives thereof.

In one embodiment, the target protein of the present invention is used in the screening assays of the present invention with a 26S proteasome and may be any protein that can structurally fit or refold within the inner chamber of a 20S proteasome. Normally the inner chamber of a 20S proteasome can structurally accommodate any protein that is 70 kD or less.

According to the present invention, a target protein is deconjugated, removed, or separated from its modifier protein by being exposed or contacted to a polypeptide having the JAB subunit or JAM domain. Such exposure or contact may be in vivo via administering the polypeptide to a subject in need of such treatment or in vitro via incubating the polypeptide with the target protein. In one embodiment, an inhibitor of a polypeptide having the JAB subunit or JAM domain can be used to increase the association of a modifier protein to a target protein in vitro or in vivo.

According to another aspect of the invention, a polypeptide having the JAB subunit or JAM domain can be used for screening assays for agents that affect the deconjugation, removal, or separation of a modifier protein from a target protein. The screening assays provided by the present invention can be carried out by incubating in the presence and absence of a test agent, a target protein, e.g., conjugated with a modifier protein and a polypeptide containing the JAB subunit or JAM domain, and determining the effect of the test agent.

Normally an increase or decrease in the amount of the target protein not conjugated to the modifier protein caused by the test agent is indicative of an agent capable of affecting deconjugation, removal, or separation of the modifier protein from the target protein. For example, a test agent decreasing the amount of the target protein not conjugated to the modifier protein is indicative of an agent decreasing the deconjugation of the modifier protein from the target protein.

In one embodiment, the polypeptide used in the screening assays provided by the present invention is a polypeptide complex of 26S proteasome while the modifier protein is ubiquitin. The polypeptide complex of 26S proteasome can be obtained by any suitable means available in the art. For example, 26S proteasome can be purified from eukaryotic cells or tissues, e.g., S. cerevisiae or human.

In another embodiment, the incubation in the presence and absence of a test agent, a target protein, and 26S proteasome of the screening assays provided by the present invention is carried out in the presence of a 20S inhibitor or an inhibitor of the degradation process associated with the de-ubiquitination process of the 26S proteasome pathway. Any 20S inhibitor or inhibitor of the degradation process can be used for the purpose of the present invention. For example, a 20S inhibitor can be MG132, lactacystin, epoxomycin, PS-349, PS-519, LLnL, or the derivatives thereof. In general, such inhibitor prevents or decreases the degradation of a target protein that is not conjugated to a modifier protein, e.g., ubiquitin.

In yet another embodiment, the incubation is conducted further in the presence of an energy source, e.g., ATP. In still another embodiment, the incubation is conducted further in the presence of an inhibitor of deubiquitination by a conventional ubiquitin isopeptidase, e.g., an ubiquitin isopeptidase other than those that associated with a JAB subunit such as 26S proteasome. One example of such inhibitor is ubiquitin aldehyde, e.g., at 2-5 µM.

The test agent used for the screening methods of the present invention can be any agent from any library of compounds or molecules. In one embodiment, the test agent is selected or derived from compounds likely to inhibit the activity of metalloproteinase, e.g., compounds having zinc-binding functionality. For example, the test agent can be any compounds having a hydroxamate moiety or a member of a hydroxamate compound library, reverse hydroxamate compound library, thiol compound library, carboxylate compound library, or phosphonic acid compound library.

According to another aspect of the present invention, the JAM domain can be used for rational drug design or as a guide for identifying agents that are capable of affecting the activity of the JAM domain or any polypeptide containing the JAM domain, e.g., identify inhibitors of the JAM domain. In one embodiment, the structure coordinates or atomic coordinates of the JAM domain or any polypeptide containing the JAM domain are used to design a potential inhibitor that will form a covalent or non-covalent bond with one or more amino acids within the JAM domain or metal ions bound by the JAM domain. In another embodiment, the potential inhibitor is designed to form a covalent bond or non-covalent bond with histidine or aspartate of the JAM domain. Such designed potential inhibitor can be synthesized by any suitable means and be tested for their ability to inhibit the activity, e.g., peptidase activity of the JAM domain.

The structure or atomic coordinates of the JAM domain or a polypeptide containing the JAM domain refer to mathematical coordinates derived from mathematical equations related to the patterns obtained on diffraction of a monochromatic beam of X-rays by the atoms (scattering centers) of the JAM domain or the polypeptide containing the JAM domain in crystal form. The diffraction data normally are used to calculate an electron density map of the repeating unit of the crystal. The electron density maps are generally used to establish the positions of the individual atoms within the unit cell of the crystal.

Various methods can be used to obtain the structure or atomic coordinates of the JAM domain or a polypeptide containing the JAM domain. For example, three dimensional diffraction data for a polypeptide containing the JAM domain can be collected at temperatures ranging from 100-274 K using an area detector and radiation from a rotating-anode X-ray generator and from the Stanford synchrotron. These data, along with data collected from a heavy atom derivative of the polypeptide, can be processed and the structure can be solved by methods which make use of the isomorphous differences between a derivative and native polypeptide and/or make use of the anomalous X-ray scattering from the heavy atom in the derivative. In one embodiment, the structure or atomic coordinates of one JAM containing polypeptide can be solved by using the phases of another JAM containing polypeptide structure or sections thereof that has already been previously determined. High resolution data sets can be solved by direct methods.

According to another aspect of the present invention, any agent that is capable of inhibiting or decreasing the deconjugation, removal, or separation of a modifier protein from a target protein can be used therapeutically to treat various conditions associated with protein regulation, e.g., de-ubiquitination or de-neddylation. For example, any agent identified by the screening methods of the present invention that is able to decrease the deconjugation of a modifier protein from a target protein, e.g., an inhibitor of the isopeptidase activity of 26S proteasome can be used therapeutically to treat neoplastic growth, angiogenesis, infection, chronic inflammation, asthma, ischemia and reperfusion injury, multiple sclerosis, rheumatoid arthritis, and psoriasis.

The agents of the present invention useful for therapeutic treatment can be administered alone, in a composition with a suitable pharmaceutical carrier, or in combination with other therapeutic agents. An effective amount of the agents to be administered can be determined on a case-by-case basis. Factors should be considered usually include age, body weight, stage of the condition, other disease conditions, duration of the treatment, and the response to the initial treatment. Typically, the agents are prepared as an injectable, either as a liquid solution or suspension. However, solid forms suitable for solution in, or suspension in, liquid vehicles prior to injection can also be prepared. The agent can also be formulated into an enteric-coated tablet or gel capsule according to known methods in the art. The agents of the present invention may be administered in any way which is medically acceptable which may depend on the disease condition or injury being treated. Possible administration routes include injections, by parenteral routes such as intravascular, intravenous, intraepidural or others, as well as oral, nasal, ophthalmic, rectal, topical, or pulmonary, e.g., by inhalation. The agents may also be directly applied to tissue surfaces, e.g., during surgery. Sustained release administration is also specifically included in the invention, by such means as depot injections or erodible implants.

EXAMPLES

The following examples are intended to illustrate but not to limit the invention in any manner, shape, or form, either explicitly or implicitly. While they are typical of those that might be used, other procedures, methodologies, or techniques known to those skilled in the art may alternatively be used.

Example 1.

De-Ubiquination by 26S Proteasome

To demonstrate that an isopeptidase activity associated with the 26S proteasome can deubiquitinate a target polypeptide in vitro, experiments were conducted to incubate multiubiquitinated Sic1 substrate (300 nM) for 0 or 5 minutes at 25° C. in the presence of purified 26S proteasome (100 nM), epoxomicin (100 μM), and ubiquitin aldehyde (5 μM).

Epoxomicin was included to uncouple the deubiquitination and degradation of a substrate by the 26S proteasome, since these two processes are normally tightly coupled. Epoxomicin forms a covalent adduct with the catalytically active N-terminal threonine residues of beta subunits of the 20S proteasome, thereby eliminating the proteolytic activity of this particle. At the end of the incubation, samples were supplemented with SDS-PAGE sample buffer, fractionated on an SDS-polyacrylamide gel, transferred to nitrocellulose, and immunoblotted with antibodies directed against Sic1. Filter-bound antibodies were decorated with goat-anti-rabbit antibody conjugated to horse radish peroxidase and visualized with ECL reagents.

This experiment demonstrated that inhibition of 20S peptidase activity is required to observe the production of deubiquitinated Sic1 by 26S proteasome. In the absence of epoxomicin, ubiquitinated Sic1 was completely degraded by the 26S proteasome. In the presence of epoxomicin, the Sic1 was not degraded, but the majority of it was deubiquitinated such that the input substrate was converted from a heterogeneous smear of >220 KD to a discrete species of ~40 KD, which corresponds to Sic1 lacking any covalently attached ubiquitin molecules.

To test if this reaction is dependent upon ATP, multiubiquitinated Sic1 substrate (300 nM) and purified 26S proteasome (100 nM) were incubated in the presence or absence of epoxomicin (100 μM), glucose (30 mM) plus hexokinase (5 U/ml), apyrase (15 U/ml), and ubiquitin vinyl sulfone (Ub-PVS; 2.5 μM) as indicated. This experiment revealed that ATP is required to observe the deubiquitination of target polypeptide by purified 26S proteasome. Specifically, in the presence of multiubiquitinated Sic1 substrate, 26S proteasome (which contains ATP), and epoxomicin, the input substrate was converted from a heterogeneous smear of >220 KD to a discrete species of ~40 KD, which corresponds to Sic1 lacking any covalently attached ubiquitin molecules. However, in the additional presence of apyrase or glucose plus hexokinase (both of which consume ATP), no deubiquitination of the multiubiquitinated Sic1 substrate was observed. This reaction was not sensitive to ubiquitin vinyl sulfone, which is an inhibitor of conventional ubiquitin isopeptidases.

These data demonstrate that the 26S proteasome recognizes a ubiquitinated substrate, and begins to translocate it into the internal cavity of the 20S proteasome, where it is degraded. As the substrate is being translocated into the 20S proteasome, the ubiquitin chains are clipped off by a previously unknown isopeptidase that is in the 26S proteasome. Under normal circumstances this is not detected because substrate degradation and removal of the ubiquitin chains occurs contemporaneously. However, in the presence of an inhibitor of the 20S peptidases, the substrate is completely deubiquitinated and translocated into the central cavity of the 20S proteasome, but is not degraded. Hence the deubiquitinated product is readily detected Mass spectrometric analysis of affinity-purified yeast 26S proteasome that is active in deubiquitinating Sic1 revealed only a single deubiquitinating enzyme: Ubp6 (Verma et al., Mol Biol Cell 11:3425 (2000)). However, 26S proteasome purified from a ubp6Δ mutant yeast strain and assayed as described above was fully competent to deubiquitinate multiubiquitinated Sic1 to yield Sic1 lacking any covalently attached ubiquitin molecules.

The above demonstrations enable an assay wherein the substrate is observed to be converted from a ubiquitinated molecule to a deubiquitinated molecule. There are many straightforward procedures by which this conversion can be monitored. For example, the removal of a multiubiquitin chain from a protein can change enzymatic, spectroscopic, fluorescent, or molecular interaction properties of the ubiquitinated protein. As one specific example, a protein that emits light e.g., luciferase will be made inactive due to the attachment of multiubiquitin chains.

The multiubiquitin chains will be attached by enzymatic, chemical, molecular genetic, or a combination of these methods. The cleavage of ubiquitin chains from the inactive luciferase substrate as it is being translocated into the inner cavity of the 20S proteasome in the presence of a 20S peptidase inhibitor will enable the luciferase to fold and thereby acquire the ability to emit light upon ATP hydrolysis.

The inner chamber of the 20S proteasome can accommodate a folded protein of approximately 70 kD. Therefore, any protein domain less than 70 kD whose enzymatic, spectroscopic, fluorescent, or molecular interaction properties can be reversibly altered by attachment of ubiquitin or a multiubiquitin chain can be used as a substrate to monitor ubiquitin isopeptidase activity of the 26S proteasome based on the methods that are disclosed herein.

Inhibition of the 26S proteasome's ability to degrade proteins by blockage of ubiquitin isopeptidase activity would be applicable to the treatment of cancer, ischemia and reperfusion injury, and diseases characterized by excessive inflammation or autoimmune responses, including asthma, rheumatoid arthritis, psoriasis, and multiple sclerosis.

To test whether the deconjugation of ubiquitin from a substrate protein is required for its degradation, we evaluated the degradation of an ubiquitin-proteasome pathway substrate in cells deficient in Rpn11-asssociated metalloprotease activity. A set of four congenic strains was generated: MPR (wild type), mpr1-1, mpr1-1 harboring an integrated copy of RPN11 in which the codons for histidine 109 and 111 have been mutated to alanine (mpr1-1 leu2::LEU2-rpn11AxA), and mpr1-1 harboring an integrated copy of wild type RPN11 (mpr1-1 leu2::LEU2-RPN11). mpr1-1 is a temperature-sensitive allele of RPN11, and complementation tests demonstrated that wild type RPN11 but not rpn11AxA was able to complement the temperature-sensitive growth defect of mpr1-1.

All of the strains described above were transformed with a plasmid that encodes $Ub^{V76}$-Val-$e^{\Delta K}$-βGal, which is an unstable protein that is degraded via the ubiquitin-proteasome pathway. All strains were pulse-radiolabeled with $^{35}$S-Translabel for 5 min at 37° C., and then at time 0 a chase was initiated by addition of 10 mM cold methionine and 500 µg/ml cycloheximide. At 7, 14, and 22 minutes following the initiation of chase, aliquots of the culture were removed and processed for immunoprecipitation with antibodies directed against β-galactosidase. Immunoprecipitated proteins were fractionated by SDS-PAGE and visualized by autoradiography.

The data demonstrated that the normally unstable Ub$^{V76}$Val-e$^{ΔK}$-βGal reporter was dramatically stabilized in mpr1-1 cells. Rapid turnover of the test protein in mpr1-1 cells was restored by an integrated copy of RPN11, but not rpn11AxA. Thus, the metalloprotease active site of Rpn11 was required for rapid turnover of proteins by the ubiquitin-proteasome pathway in vivo.

This result was further confirmed in vitro. We demonstrated that purified 26S proteasomes that lack critical metalloprotease active site residues of Rpn11 were unable to deubiquitinate and degrade ubiquitinated Sic1. 26S proteasomes were affinity-purified from *Saccharomyces cerevisiae* cells in which the PRE1 gene was modified to encode a Pre1 polypeptide tagged with a FLAG epitope, as described (Verma et al., 2000 Mol Biol Cell 11:3425).

Wild type 26S proteasome was purified from a strain with the genotype pre1::PRE1-FLAG-HIS6 (URA3) his3-11 ade2-1 112 trp1-Δ2 can1-100, mpr1-1, leu2::LEU2-RPN11, and mutant 26S proteasome was purified from a strain with the genotype pre1::PRE1-FLAG-HIS6 (URA3) his3-11 ade2-1 112 trp1-Δ2 can1-100, mpr1-1, leu2::LEU2-rpn11AXA.

Purified proteasomes were evaluated by immunoblotting with antibodies directed against *Schizosaccharomyces pombe* Pad1, which cross-reacted with Rpn11. Wild type and point mutant Rpn11 polypeptides were readily distinguished from Mpr1-1 polypeptide, because the latter is truncated due to a frameshift mutation. The immunoblot analysis revealed that both wild type and mutant proteasomes contained only full-length Rpn11 polypeptide, and none of the truncated Mpr1-1 polypeptide was detected. Thus, the results we obtained are directly attributable to the properties of the Rpn11 and Rpn11AxA proteins since no Mpr1-1 protein is present. Mass spectrometric analysis confirmed that the wild type and mutant proteasomes were of equal composition, and all subunits were present.

To evaluate their activity, wild type and Rpn11AxA mutant 26S proteasomes (100 nM) were incubated with ubiquitinated Sic1 (300 nM) plus ATP (2 mM) in the presence or absence of 100 µM epoxomicin for 0 or 5 minutes at 25° C., as indicated. Reactions were terminated by the addition of SDS-PAGE sample buffer, fractionated by SDS-PAGE, transferred to nitrocellulose, and immunoblotted with antibodies directed against Sic1. Filter-bound antibodies were decorated with goat-anti-rabbit antibody conjugated to horse radish peroxidase and visualized with ECL reagents. The data demonstrated that mutant proteasomes were unable to degrade multiubiquitinated Sic1 even in the absence of epoxomicin, and were unable to deubiquitinate multiubiquitinated Sic1 (ie to convert multiubiquitinated Sic1 from a heterogeneous smear of >220 KD to a discrete species of ~40 KD, which corresponds to Sic1 lacking any covalently attached ubiquitin molecules) in the presence of epoxomicin.

Example 2

De-Neddylation by COP9 Signalsome (CSN)

To identify a putative active site within the CSN complex that might mediate its ability to promote the cleavage of Nedd8-cullin conjugates, we subjected all eight known subunits of the CSN to sequence analysis by computer. Detailed inspection revealed that the Jab1 subunit contains conserved histidines and a conserved aspartic acid that are reminiscent of zinc-coordinating residues in a metallo-beta-lactamase. An alignment of these residues is presented in FIG. 3.

On the basis of this analysis, we hypothesized that CSN represents the founding member of a novel class of metalloproteases. To test this hypothesis, we performed the following experiments. First, we evaluated the effect of a divalent cation chelator on the Nedd8 conjugate cleavage activity associated with CSN. Mutant csn5Δ *S. pombe* cell extract that contained neddylated Pcu1 was incubated with either no additions (−) or following addition (+) of wild type lysate (which contained active CSN) supplemented with either methanol vehicle (MeOH), 1 mM 1,10-phenanthroline (O-PT), or 1 mM, 10 mM, or 20 mM EDTA. Reactions were incubated 30 minutes at 30° C. and terminated by addition of SDS-PAGE sample buffer, fractionated on an SDS-polyacrylamide gel, transferred to nitrocellulose, and immunoblotted with antibodies directed against *S. pombe* Cul1. Filter-bound antibodies were decorated with goat-anti-rabbit antibody conjugated to horse radish peroxidase and visualized with ECL reagents (Lyapina, S., et al., Science 18:1382-5 (2001)).

The data demonstrated that no inhibition was seen with 1 mM EDTA, and less than 50% inhibition was seen with 10 mM EDTA. However, 20 mM EDTA almost completely inhibited the reaction. In the context of this description, 'inhibition' means that Nedd8 was not deconjugated from Cul1 upon addition of CSN, whereas 'no inhibition' means that Nedd8 was efficiently deconjugated from Cul1 upon addition of CSN. The status of Nedd8 conjugation to Cul1 was determined by the mobility of Cul1 on the SDS-polyacrylamide gel. Nedd8-conjugated Cul1 migrated more slowly than unmodified Cul.

It is known that some metal-dependent enzymes are relatively insensitive to inhibition by EDTA, but are nevertheless potently inhibited by the chelator 1,10-phenanthroline. Intriguingly, 1,10-phenanthroline at 1 mM completeley inhibited the Nedd8 conjugate cleavage activity of CSN. Thus, biochemical data suggested that CSN is in fact a metalloprotease.

To further confirm the hypothesis that arose from our sequence analysis, we individually mutated the conserved histidines and aspartic acid in *Schizosaccharomyces pombe* csn5+, and tested the ability of each point-mutated gene to complement the cullin deneddylation defect of a csn5Δ mutant (Lyapina, S., et al., Science 18:1382-5 (2001); Zhou, C., et al., BMC Biochemistry 2:7 (2001)). Wild type *S. pombe* csn5+ and the indicated mutant derivatives were inserted into the *S. pombe* expression vector pREP41 and transfected into *S. pombe* csn5Δ cells.

Transformants were evaluated for modification state of Pcu1 by fractionating cell extracts on an SDS-polyacrylamide gel, transferring fractionated proteins to nitrocellulose, and immunoblotting with antibodies directed against *S. pombe* Cul1. Filter-bound antibodies were decorated with goat-anti-rabbit antibody conjugated to horse radish peroxidase and visualized with ECL reagents.

The data from this experiment demonstrated that csn5Δ cells that contained empty vector accumulated Pcu1 exclusively in the Nedd8-modified form. This accumulation was reversed upon expression of wild type csn5+, but not the H118A, H120A, and D131N mutants. Thus, the putative active site residues identified by computer analysis are absolutely required for CSN activity in deconjugating Nedd8 from Cul1 in vivo.

Based on the data described above, we conclude that CSN is a novel metalloprotease. The active site of CSN resides, at least in part, in the Jab1/Csn5 subunit, and this active site is proposed to bind a metal ion which initiates hydrolytic attack of the isopeptide bonds cleaved by CSN. These findings enable the development of targeted screens for compounds that inhibit or enhance the catalytic activity of CSN, and also allow for the rationale design of compounds that modulate CSN activity based on knowledge of the mechanism of action of other metalloenzymes.

Finally, this knowledge might be used for two further purposes. First, we suggest it should be possible to re-engineer the specificity of CSN, Jab1, or related proteins to create novel isopeptidases with desired specificities. Such enzymes might be useful in a variety of applications involving the cleavage of protein cross-links or conjugates. Second, it should be possible to isolate or design compounds that inhibit the prokaryotic homologs of Csn5/Jab1. These inhibitors may have a number of applications, including use as antibiotics.

We have also tested the role of Cys box (Cys 145) in association with CSN's ability to deconjugate Nedd8 from Cul1, using an in vitro deconjugation assay as described above. The experimental data demonstrate that a Jab1 mutant in which the conserved cysteine of the Cys box (Cys 145) is mutated to alanine has wild-type levels of Nedd8 conjugate cleavage activity.

Example 3

AMSH, AMSH1, and AMSH2

As discussed above, we have documented the existence of a novel metalloprotease active site motif that we have dubbed the JAM domain (for Jab1-associated metalloenzyme motif). The Rpn11 subunit of the 26S proteosome and the Csn5 subunit of the COP9-signalosome (CSN) both contain a JAM domain. We have provided direct evidence that the JAM domain of Csn5 is essential for the Nedd8 isopeptidase activity of CSN, and the JAM domain of Rpn11 is essential for the ubiquitin isopeptidase activity of the 26S proteosome.

Our data teach that eukaryotic JAM domain proteins contain isopeptidase activity that deconjugate modifier proteins from target proteins, wherein the carboxy terminus of the modifier protein is attached via a peptide bond to a free amino group of the target protein, including but not restricted to the amino terminus and the epsilon amino group of lysine residues in the target protein.

In addition to Csn5 and Rpn11, there are many proteins expressed in human cells that contain an intact JAM domain. (see Table 1) The AMSH proteins have been implicated in cytokine signaling, TGF-b signaling, and survival of hippocampal neurons (Ishii, N., et al., Mol Cell Biol. 24:8626-37 (2001); Itoh, F., et al., EMBO J. 15:4132-42 (2001); Tanaka, N., et al., J Biol Chem. 27:19129-35 (1999)).

Our data teach that the histidine 335, histidine 337, and aspartate 348 residues of AMSH (and the equivalent residues in AMSH1 and AMSH2, see FIG. 2) specify a metalloprotease active site. Furthermore, our data teach that compounds that inhibit the active site specified by these residues will inhibit the ability of AMSH, AMSH1, and AMSH2 to deconjugate a modifier protein from a target protein, wherein the modifier protein includes NEDD8, UBL1, SMT3H2, SMT3H1, APG12, FAT10, Fau, UCRP/ISG15, URM1, or UBL5.

Although the invention has been described with reference to the presently preferred embodiment, it should be understood that various modifications can be made without departing from the spirit of the invention. Accordingly, the invention is limited only by the following claims.

What is claimed is:

1. A method of identifying an agent that affects isopeptidase activity of an Rpn11 polypeptide having the amino acid sequence of SEQ ID NO:23 or 24 comprising:
incubating a test agent with the Rpn11 polypeptide in the presence of a modifier protein and a target protein, wherein the Rpn11 polypeptide has isopeptidase activity and deconjugates the modifier protein from the target protein; and
determining the isopeptidase activity of the polypeptide—by measuring deconjugation of the modifier protein from the target protein in the presence and absence of the test agent, wherein a difference in the isopeptidase activity in the presence versus the absence of the test agent is indicative of an agent that affects isopeptidase activity of the Rpn11 polypeptide, wherein the modifier protein is a ubiquitin or a ubiquitin-like modifier protein.

2. The method of claim 1, wherein the Rpn11 polypeptide has a JAMM domain consisting essentially of the amino acid sequence of GW(Y/I)H(S/T)HPXXXXXXSXXD (SEQ ID NO. 2), wherein G is glycine, W is tryptophan, Y is tyrosine, I is isoleucine, H is histidine, S is serine, T is threonine, P is proline, D is aspartate, X is any amino acid, Y/I is either Y or I, and S/T is either S or T.

3. The method of claim 1, wherein the target protein has ubiquitin ligase activity.

4. The method of claim 1, wherein the target protein is part of a protein complex having ubiquitin ligase activity.

5. The method of claim 1, wherein an increase in the amount of the target protein not conjugated to the modifier protein is indicative of an agent that increases deconjugation of the modifier protein from the target protein.

6. The method of claim 1, wherein the target protein or modifier protein, or both, comprise a detectable label.

7. The method of claim 1, wherein the target protein is a fluorescent protein.

8. The method of claim 7, wherein the fluorescent protein is selected from the group consisting of green fluorescent protein, yellow fluorescent protein, cyan fluorescent protein and dsRed.

9. The method of claim 7, wherein the label has the activity of peroxidase, alkaline phosphatase, or luciferase.

10. The method of claim 1, wherein the target protein causes production of a detectable signal upon deconjugation from the modifier protein.

11. The method of claim 1, wherein Rpn11 is a polypeptide of a 26S proteasome.

12. The method of claim 1, wherein Rpn11 is a polypeptide of a 26S proteasome and the modifier protein is an ubiquitin.

13. The method of claim 11, wherein the incubation is conducted in the presence and absence of the test agent, the target protein, and a 20S inhibitor.

14. The method of claim 11, wherein the incubation is further conducted in the presence and absence of the test agent, the target protein, a 20S inhibitor, and ATP.

15. The method of claim 11, wherein the target protein not conjugated to the modifier protein is not degraded.

16. The method of claim 11, wherein the target protein is Sic1.

17. The method of claim 11, wherein the 26S proteasome is purified from *S. cerevisiae*.

18. The method of claim 11, wherein the 26S proteasome is purified from eukaryotic cells.

19. The method of claim 11, wherein the 26S proteasome is purified from human cells.

20. The method of claim 1, wherein the test agent is a member of a compound library selected from the group consisting of hydroxamate compound library, reverse hydroxamate compound library, carboxylate compound library, thiol compound library, and phosphonate compound library.

21. The method of claim 1, wherein the method further comprises carrying out the incubation in the presence of an inhibitor of degradation of the target protein.

22. The method of claim 1, further comprising after the incubation, determining whether the modifier protein remains conjugated to the target protein via a peptide bond formed between the carboxy terminus of the modifier protein and a free amino group of the target protein.

23. A method of identifying an agent that affects isopeptidase activity of an AMSH polypeptide having the amino acid sequence of SEQ ID NO:7 comprising:
    incubating a test agent with the AMSH polypeptide in the presence of a modifier protein and a target protein, wherein the AMSH polypeptide isopeptidase activity and deconjugates the modifier protein from the target protein; and
    determining the isopeptidase activity of the polypeptide by measuring deconjugation of the modifier protein from the target protein in the presence and absence of the test agent, wherein a difference in the isopeptidase activity in the presence versus the absence of the test agent is indicative of an agent that affects isopeptidase activity of the AMSH polypeptide, wherein the modifier protein is a ubiquitin or a ubiquitin-like modifier protein.

24. The method of claim 23, wherein the polypeptide comprises a JAMM domain comprises AMSH1 and/or AMSH2.

* * * * *

SEQUENCE LISTING

```
<160> NUMBER OF SEQ ID NOS: 22

<210> SEQ ID NO 1
<211> LENGTH: 14
<212> TYPE: PRT
<213> ORGANISM: Artificial sequence
<220> FEATURE:
<223> OTHER INFORMATION: JAM domain
<221> NAME/KEY: MISC_FEATURE
<222> LOCATION: (1)..(14)
<223> OTHER INFORMATION: Xaa is any amino acid

<400> SEQUENCE: 1

His Xaa His Xaa Xaa Xaa Xaa Xaa Xaa Xaa Xaa Xaa Xaa Asp
1               5                   10

<210> SEQ ID NO 2
<211> LENGTH: 17
<212> TYPE: PRT
<213> ORGANISM: Artificial sequence
<220> FEATURE:
<223> OTHER INFORMATION: JAM domain
<221> NAME/KEY: MISC_FEATURE
<222> LOCATION: (3)..(3)
```

```
<223> OTHER INFORMATION: Xaa is Tyr or Ile
<221> NAME/KEY: MISC_FEATURE
<222> LOCATION: (5)..(5)
<223> OTHER INFORMATION: Xaa is Ser or Thr
<221> NAME/KEY: MISC_FEATURE
<222> LOCATION: (8)..(16)
<223> OTHER INFORMATION: Xaa is any amino acid

<400> SEQUENCE: 2

Gly Trp Xaa His Xaa His Pro Xaa Xaa Xaa Xaa Xaa Ser Xaa Xaa
1               5                   10                  15
Asp

<210> SEQ ID NO 3
<211> LENGTH: 246
<212> TYPE: PRT
<213> ORGANISM: Homo sapiens

<400> SEQUENCE: 3

Thr Met Ile Ile Met Asp Ser Phe Ala Leu Pro Val Glu Gly Thr Glu
1               5                   10                  15

Thr Arg Val Asn Ala Gln Ala Ala Tyr Glu Tyr Met Ala Ala Tyr
            20                  25                  30

Ile Glu Asn Ala Lys Gln Val Gly Arg Leu Glu Asn Ala Ile Gly Trp
            35                  40                  45

Tyr His Ser His Pro Gly Tyr Gly Cys Trp Leu Ser Gly Ile Asp Val
        50                  55                  60

Ser Thr Gln Met Leu Asn Gln Gln Phe Gln Glu Pro Phe Val Ala Val
65                  70                  75                  80

Val Ile Asp Pro Thr Arg Thr Ile Ser Ala Gly Lys Val Asn Leu Gly
                85                  90                  95

Ala Phe Arg Thr Tyr Pro Lys Gly Tyr Lys Pro Pro Asp Glu Gly Pro
                100                 105                 110

Ser Glu Tyr Gln Thr Ile Pro Leu Asn Lys Ile Glu Asp Phe Gly Val
                115                 120                 125

His Cys Lys Gln Tyr Tyr Ala Leu Glu Val Ser Tyr Phe Lys Ser Ser
    130                 135                 140

Leu Asp Arg Lys Leu Leu Glu Leu Leu Trp Asn Lys Tyr Trp Val Asn
145                 150                 155                 160

Thr Leu Ser Ser Ser Leu Leu Thr Asn Ala Asp Tyr Thr Thr Gly
                165                 170                 175

Gln Val Phe Asp Leu Ser Glu Lys Leu Glu Gln Ser Glu Ala Gln Leu
                180                 185                 190

Gly Arg Gly Ser Phe Met Leu Gly Leu Glu Thr His Asp Arg Lys Ser
            195                 200                 205

Glu Asp Lys Leu Ala Lys Ala Thr Arg Asp Ser Cys Lys Thr Thr Ile
    210                 215                 220

Glu Ala Ile His Gly Leu Met Ser Gln Val Ile Lys Asp Lys Leu Phe
225                 230                 235                 240

Asn Gln Ile Asn Ile Ser
                245

<210> SEQ ID NO 4
<211> LENGTH: 245
<212> TYPE: PRT
<213> ORGANISM: Homo sapiens

<400> SEQUENCE: 4

Thr Val Arg Val Ile Asp Val Phe Ala Met Pro Gln Ser Gly Thr Gly
```

```
1               5                   10                  15
Val Ser Val Glu Ala Val Asp Pro Val Phe Gln Ala Lys Met Leu Asp
                20                  25                  30

Met Leu Lys Gln Thr Gly Arg Pro Glu Met Val Val Gly Trp Tyr His
                35                  40                  45

Ser His Pro Gly Phe Gly Cys Trp Leu Ser Gly Val Asp Ile Asn Thr
        50                  55                  60

Gln Gln Ser Phe Glu Ala Leu Ser Glu Arg Ala Val Ala Val Val Val
65                  70                  75                  80

Asp Pro Ile Gln Ser Val Lys Gly Lys Val Val Ile Asp Ala Phe Arg
                85                  90                  95

Leu Ile Asn Ala Asn Met Met Val Leu Gly His Glu Pro Arg Gln Thr
                100                 105                 110

Thr Ser Asn Leu Gly His Leu Asn Lys Pro Ser Ile Gln Ala Leu Ile
        115                 120                 125

His Gly Leu Asn Arg His Tyr Tyr Ser Ile Thr Ile Asn Tyr Arg Lys
    130                 135                 140

Asn Glu Leu Glu Gln Lys Met Leu Leu Asn Leu His Lys Lys Ser Trp
145                 150                 155                 160

Met Glu Gly Leu Thr Leu Gln Asp Tyr Ser Glu His Cys Lys His Asn
                165                 170                 175

Glu Ser Val Val Lys Glu Met Leu Glu Leu Ala Lys Asn Tyr Asn Lys
                180                 185                 190

Ala Val Glu Glu Asp Lys Met Thr Pro Gln Leu Ala Ile Lys
                195                 200                 205

Asn Val Gly Lys Gln Asp Pro Lys Arg His Leu Glu Glu His Val Asp
    210                 215                 220

Val Leu Met Thr Ser Asn Ile Val Gln Cys Leu Ala Ala Met Leu Asp
225                 230                 235                 240

Thr Val Val Phe Lys
            245

<210> SEQ ID NO 5
<211> LENGTH: 421
<212> TYPE: PRT
<213> ORGANISM: Homo sapiens

<400> SEQUENCE: 5

Met Pro Asp His Thr Asp Val Ser Leu Ser Pro Glu Glu Arg Val Arg
1               5                   10                  15

Ala Leu Ser Lys Leu Gly Cys Asn Ile Thr Ile Ser Glu Asp Ile Thr
                20                  25                  30

Pro Arg Arg Tyr Phe Arg Ser Gly Val Glu Met Glu Arg Met Ala Ser
                35                  40                  45

Val Tyr Leu Glu Glu Gly Asn Leu Glu Asn Ala Phe Val Leu Tyr Asn
        50                  55                  60

Lys Phe Ile Thr Leu Phe Val Glu Lys Leu Pro Asn His Arg Asp Tyr
65                  70                  75                  80

Gln Gln Cys Ala Val Pro Glu Lys Gln Asp Ile Met Lys Lys Leu Lys
                85                  90                  95

Glu Ile Ala Phe Pro Arg Thr Asp Glu Leu Lys Asn Asp Leu Leu Lys
                100                 105                 110

Lys Tyr Asn Val Glu Tyr Gln Glu Tyr Leu Gln Ser Lys Asn Lys Tyr
        115                 120                 125
```

```
Lys Ala Glu Ile Leu Lys Lys Leu Glu His Gln Arg Leu Ile Glu Ala
            130                 135                 140

Glu Arg Lys Arg Ile Ala Gln Met Arg Gln Gln Leu Glu Ser Glu
145                 150                 155                 160

Gln Phe Leu Phe Glu Asp Gln Leu Lys Lys Gln Glu Leu Ala Arg
                165                 170                 175

Gly Gln Met Arg Ser Gln Gln Thr Ser Gly Leu Ser Glu Gln Ile Asp
                180                 185                 190

Gly Ser Ala Leu Ser Cys Phe Ser Thr His Gln Asn Asn Ser Leu Leu
                195                 200                 205

Asn Val Phe Ala Asp Gln Pro Asn Lys Ser Asp Ala Thr Asn Tyr Ala
        210                 215                 220

Ser His Ser Pro Pro Val Asn Arg Ala Leu Thr Pro Ala Ala Thr Leu
225                 230                 235                 240

Ser Ala Val Gln Asn Leu Val Val Gly Leu Arg Cys Val Val Leu
                245                 250                 255

Pro Glu Asp Leu Cys His Lys Phe Leu Gln Leu Ala Glu Ser Asn Thr
                260                 265                 270

Val Arg Gly Ile Glu Thr Cys Gly Ile Leu Cys Gly Lys Leu Thr His
                275                 280                 285

Asn Glu Phe Thr Ile Thr His Val Ile Val Pro Lys Gln Ser Ala Gly
        290                 295                 300

Pro Asp Tyr Cys Asp Met Glu Asn Val Glu Glu Leu Phe Asn Val Gln
305                 310                 315                 320

Asp Gln His Asp Leu Leu Thr Leu Gly Trp Ile His Thr His Pro Thr
                325                 330                 335

Gln Thr Ala Phe Leu Ser Ser Val Asp Leu His Thr His Cys Ser Tyr
                340                 345                 350

Gln Leu Met Leu Pro Glu Ala Ile Ala Ile Val Cys Ser Pro Lys His
                355                 360                 365

Lys Asp Thr Gly Ile Phe Arg Leu Thr Asn Ala Gly Met Leu Glu Val
        370                 375                 380

Ser Ala Cys Lys Lys Gly Phe His Pro His Thr Lys Glu Pro Arg
385                 390                 395                 400

Leu Phe Ser Ile Cys Lys His Val Leu Val Lys Asp Ile Lys Ile Ile
                405                 410                 415

Val Leu Asp Leu Arg
            420

<210> SEQ ID NO 6
<211> LENGTH: 461
<212> TYPE: PRT
<213> ORGANISM: Homo sapiens

<400> SEQUENCE: 6

Met Asp Gln Pro Phe Thr Val Asn Ser Leu Lys Lys Leu Ala Ala Met
1               5                   10                  15

Pro Asp His Thr Asp Val Ser Leu Ser Pro Glu Glu Arg Val Arg Ala
                20                  25                  30

Leu Ser Lys Leu Gly Cys Asn Ile Thr Ile Ser Glu Asp Ile Thr Pro
            35                  40                  45

Arg Arg Tyr Phe Arg Ser Gly Val Glu Met Glu Arg Met Ala Ser Val
        50                  55                  60

Tyr Leu Glu Glu Gly Asn Leu Glu Asn Ala Phe Val Leu Tyr Asn Lys
65                  70                  75                  80
```

```
Phe Ile Thr Leu Phe Val Glu Lys Leu Pro Asn His Arg Asp Tyr Gln
                85                  90                  95

Gln Cys Ala Val Pro Glu Lys Gln Asp Ile Met Lys Lys Leu Lys Glu
            100                 105                 110

Ile Ala Phe Pro Arg Thr Asp Glu Leu Lys Asn Asp Leu Leu Lys Lys
            115                 120                 125

Tyr Asn Val Glu Tyr Gln Glu Tyr Leu Gln Ser Lys Asn Lys Tyr Lys
            130                 135                 140

Ala Glu Ile Leu Lys Lys Leu Glu His Gln Arg Leu Ile Glu Ala Glu
145                 150                 155                 160

Arg Lys Arg Ile Ala Gln Met Arg Gln Gln Leu Glu Ser Glu Gln
            165                 170                 175

Phe Leu Phe Glu Asp Gln Leu Lys Lys Gln Glu Leu Ala Arg Gly
            180                 185                 190

Gln Met Arg Ser Gln Gln Thr Ser Gly Leu Ser Glu Gln Ile Asp Gly
            195                 200                 205

Ser Ala Leu Ser Cys Phe Ser Thr His Gln Asn Asn Ser Leu Leu Asn
    210                 215                 220

Val Phe Ala Asp Gln Pro Asn Lys Ser Asp Ala Thr Asn Tyr Ala Ser
225                 230                 235                 240

His Ser Pro Pro Val Asn Arg Ala Leu Thr Pro Ala Ala Thr Leu Ser
                245                 250                 255

Ala Val Gln Asn Leu Val Val Glu Gly Leu Arg Cys Val Val Leu Pro
            260                 265                 270

Glu Asp Leu Cys His Lys Phe Leu Gln Leu Ala Glu Ser Asn Thr Val
            275                 280                 285

Arg Gly Ile Glu Thr Cys Gly Ile Leu Cys Gly Lys Leu Thr His Asn
            290                 295                 300

Glu Phe Thr Ile Thr His Val Ile Val Pro Lys Gln Ser Ala Gly Pro
305                 310                 315                 320

Asp Tyr Cys Asp Met Glu Asn Val Glu Glu Leu Phe Asn Val Gln Asp
                325                 330                 335

Gln His Asp Leu Leu Thr Leu Gly Trp Ile His Thr His Pro Thr Gln
            340                 345                 350

Thr Ala Phe Leu Ser Ser Val Asp Leu His Thr His Cys Ser Tyr Gln
            355                 360                 365

Leu Met Leu Pro Glu Ala Ile Ala Ile Val Cys Ser Pro Lys His Lys
            370                 375                 380

Asp Thr Gly Ile Phe Arg Leu Thr Asn Ala Gly Met Leu Glu Val Ser
385                 390                 395                 400

Ala Cys Lys Lys Lys Gly Phe His Pro His Thr Lys Glu Pro Arg Leu
                405                 410                 415

Phe Ser Ile Gln Lys Phe Leu Ser Gly Ile Ser Gly Thr Ala Leu
            420                 425                 430

Glu Met Glu Pro Leu Lys Ile Gly Tyr Gly Pro Asn Gly Phe Pro Leu
            435                 440                 445

Leu Gly Ile Ser Arg Ser Ser Ser Pro Ser Glu Gln Leu
    450                 455                 460

<210> SEQ ID NO 7
<211> LENGTH: 424
<212> TYPE: PRT
<213> ORGANISM: Homo sapiens
```

<400> SEQUENCE: 7

```
Met Ser Asp His Gly Asp Val Ser Leu Pro Pro Glu Asp Arg Val Arg
1               5                   10                  15

Ala Leu Ser Gln Leu Gly Ser Ala Val Glu Val Asn Glu Asp Ile Pro
            20                  25                  30

Pro Arg Arg Tyr Phe Arg Ser Gly Val Glu Ile Ile Arg Met Ala Ser
        35                  40                  45

Ile Tyr Ser Glu Glu Gly Asn Ile Glu His Ala Phe Ile Leu Tyr Asn
    50                  55                  60

Lys Tyr Ile Thr Leu Phe Ile Glu Lys Leu Pro Lys His Arg Asp Tyr
65              70                  75                  80

Lys Ser Ala Val Ile Pro Glu Lys Lys Asp Thr Val Lys Lys Leu Lys
                85                  90                  95

Glu Ile Ala Phe Pro Lys Ala Glu Glu Leu Lys Ala Glu Leu Leu Lys
            100                 105                 110

Arg Tyr Thr Lys Glu Tyr Thr Glu Tyr Asn Glu Lys Lys Lys Lys Glu
        115                 120                 125

Ala Glu Glu Leu Ala Arg Asn Met Ala Ile Gln Gln Glu Leu Glu Lys
    130                 135                 140

Glu Lys Gln Arg Val Ala Gln Gln Lys Gln Gln Gln Leu Glu Gln Glu
145             150                 155                 160

Gln Phe His Ala Phe Glu Met Ile Arg Asn Gln Glu Leu Glu Lys
                165                 170                 175

Glu Arg Leu Lys Ile Val Gln Glu Phe Gly Lys Val Asp Pro Gly Leu
            180                 185                 190

Gly Gly Pro Leu Val Pro Asp Leu Glu Lys Pro Ser Leu Asp Val Phe
        195                 200                 205

Pro Thr Leu Thr Val Ser Ser Ile Gln Pro Ser Asp Cys His Thr Thr
    210                 215                 220

Val Arg Pro Ala Lys Pro Pro Val Val Asp Arg Ser Leu Lys Pro Gly
225             230                 235                 240

Ala Leu Ser Asn Ser Glu Ser Ile Pro Thr Ile Asp Gly Leu Arg His
                245                 250                 255

Val Val Val Pro Gly Arg Leu Cys Pro Gln Phe Leu Gln Leu Ala Ser
            260                 265                 270

Ala Asn Thr Ala Arg Gly Val Glu Thr Cys Gly Ile Leu Cys Gly Lys
        275                 280                 285

Leu Met Arg Asn Glu Phe Thr Ile Thr His Val Leu Ile Pro Lys Gln
    290                 295                 300

Ser Ala Gly Ser Asp Tyr Cys Asn Thr Glu Asn Glu Glu Glu Leu Phe
305             310                 315                 320

Leu Ile Gln Asp Gln Gln Gly Leu Ile Thr Leu Gly Trp Ile His Thr
                325                 330                 335

His Pro Thr Gln Thr Ala Phe Leu Ser Ser Val Asp Leu His Thr His
            340                 345                 350

Cys Ser Tyr Gln Met Met Leu Pro Glu Ser Val Ala Ile Val Cys Ser
        355                 360                 365

Pro Lys Phe Gln Glu Thr Gly Phe Phe Lys Leu Thr Asp His Gly Leu
    370                 375                 380

Glu Glu Ile Ser Ser Cys Arg Gln Lys Gly Phe His Pro His Ser Lys
385             390                 395                 400

Asp Pro Pro Leu Phe Cys Ser Cys Ser His Val Thr Val Val Asp Arg
                405                 410                 415
```

```
Ala Val Thr Ile Thr Asp Leu Arg
            420

<210> SEQ ID NO 8
<211> LENGTH: 58
<212> TYPE: PRT
<213> ORGANISM: Homo sapiens

<400> SEQUENCE: 8

Val Gly Arg Leu Glu Asn Ala Ile Gly Trp Tyr His Ser His Pro Gly
1               5                   10                  15

Tyr Gly Cys Trp Leu Ser Gly Ile Asp Val Ser Thr Gln Met Leu Asn
            20                  25                  30

Gln Gln Phe Gln Glu Pro Phe Val Ala Val Ile Asp Pro Thr Arg
        35                  40                  45

Thr Ile Ser Ala Gly Lys Val Asn Leu Gly
    50                  55

<210> SEQ ID NO 9
<211> LENGTH: 58
<212> TYPE: PRT
<213> ORGANISM: Drosophila melanogaster

<400> SEQUENCE: 9

Val Gly Arg Met Glu His Ala Val Gly Trp Tyr His Ser His Pro Gly
1               5                   10                  15

Tyr Gly Cys Trp Leu Ser Gly Ile Asn Val Ser Thr Gln Met Leu Asn
            20                  25                  30

Gln Thr Tyr Gln Glu Pro Phe Val Ala Ile Val Asp Pro Val Arg
        35                  40                  45

Thr Val Ser Ala Gly Lys Val Cys Leu Gly
    50                  55

<210> SEQ ID NO 10
<211> LENGTH: 58
<212> TYPE: PRT
<213> ORGANISM: Arabidopsis thaliana

<400> SEQUENCE: 10

Ala Gly Arg Leu Glu Asn Val Val Gly Trp Tyr His Ser His Pro Gly
1               5                   10                  15

Tyr Gly Cys Trp Leu Ser Gly Ile Asp Val Ser Thr Gln Arg Leu Asn
            20                  25                  30

Gln Gln His Gln Glu Pro Phe Leu Ala Val Ile Asp Pro Thr Arg
        35                  40                  45

Thr Val Ser Ala Gly Lys Val Glu Ile Gly
    50                  55

<210> SEQ ID NO 11
<211> LENGTH: 58
<212> TYPE: PRT
<213> ORGANISM: Caenorhabditis elegans

<400> SEQUENCE: 11

Glu Gly Arg Lys Glu Lys Val Val Gly Trp Tyr His Ser His Pro Gly
1               5                   10                  15

Tyr Gly Cys Trp Leu Ser Gly Ile Asp Val Ser Thr Gln Thr Leu Asn
            20                  25                  30

Gln Lys Phe Gln Glu Pro Trp Val Ala Ile Val Ile Asp Pro Leu Arg
```

```
                35                  40                  45
Thr Met Ser Ala Gly Lys Val Asp Ile Gly
    50                  55

<210> SEQ ID NO 12
<211> LENGTH: 58
<212> TYPE: PRT
<213> ORGANISM: Archaeoglobus fulgidus

<400> SEQUENCE: 12

Leu Pro Ile Gly Met Lys Val Phe Gly Thr Val His Ser His Pro Ser
1               5                   10                  15

Pro Ser Cys Arg Pro Ser Glu Glu Asp Leu Ser Leu Phe Thr Arg Phe
            20                  25                  30

Gly Lys Tyr His Ile Ile Val Cys Tyr Pro Tyr Asp Glu Asn Ser Trp
        35                  40                  45

Lys Cys Tyr Asn Arg Lys Gly Glu Glu Val
    50                  55

<210> SEQ ID NO 13
<211> LENGTH: 58
<212> TYPE: PRT
<213> ORGANISM: Pyrococcus horikoshii

<400> SEQUENCE: 13

Met Pro His Asp Glu Ser Ile Lys Gly Thr Phe His Ser His Pro Ser
1               5                   10                  15

Pro Phe Pro Tyr Pro Ser Glu Gly Asp Leu Met Phe Phe Ser Lys Phe
            20                  25                  30

Gly Gly Ile His Ile Ile Ala Ala Phe Pro Tyr Asp Glu Asp Ser Val
        35                  40                  45

Lys Ala Phe Asp Ser Glu Gly Arg Glu Val
    50                  55

<210> SEQ ID NO 14
<211> LENGTH: 58
<212> TYPE: PRT
<213> ORGANISM: Thermoplasma volcanium

<400> SEQUENCE: 14

Lys Pro Ile Asp Phe Ser Leu Val Gly Ser Val His Ser His Pro Ser
1               5                   10                  15

Gly Ile Thr Lys Pro Ser Asp Glu Asp Leu Arg Met Phe Ser Leu Thr
            20                  25                  30

Gly Lys Ile His Ile Ile Val Gly Tyr Pro Tyr Asn Leu Lys Asp Tyr
        35                  40                  45

Ser Ala Tyr Asp Arg Ser Gly Asn Lys Val
    50                  55

<210> SEQ ID NO 15
<211> LENGTH: 58
<212> TYPE: PRT
<213> ORGANISM: Methanobacterium thermoautotrophicum

<400> SEQUENCE: 15

Leu Pro Pro Phe Thr Gly Ala Val Gly Ser Val His Ser His Pro Gly
1               5                   10                  15

Pro Val Asn Leu Pro Ser Ala Ala Asp Leu His Phe Phe Ser Lys Asn
            20                  25                  30
```

```
Gly Leu Phe His Leu Ile Ile Ala His Pro Tyr Thr Met Glu Thr Val
            35                  40                  45

Ala Ala Tyr Thr Arg Asn Gly Asp Pro Val
    50                  55
```

<210> SEQ ID NO 16
<211> LENGTH: 58
<212> TYPE: PRT
<213> ORGANISM: Aquifex aeolicus

<400> SEQUENCE: 16

```
Ile Ser Lys Gly Met Glu Ile Val Gly Val Tyr His Ser His Pro Asp
1               5                   10                  15

His Pro Asp Arg Pro Ser Gln Phe Asp Leu Gln Arg Ala Phe Pro Asp
            20                  25                  30

Leu Ser Tyr Ile Ile Phe Ser Val Gln Lys Gly Lys Val Ala Ser Tyr
            35                  40                  45

Arg Ser Trp Glu Leu Lys Gly Asp Lys Phe
    50                  55
```

<210> SEQ ID NO 17
<211> LENGTH: 60
<212> TYPE: PRT
<213> ORGANISM: Mycobacterium tuberculosis

<400> SEQUENCE: 17

```
Glu Asp Ala Asp Glu Val Pro Val Val Ile Tyr His Ser His Thr Ala
1               5                   10                  15

Thr Glu Ala Tyr Pro Ser Arg Thr Asp Val Lys Leu Ala Thr Glu Pro
            20                  25                  30

Asp Ala His Tyr Val Leu Val Ser Thr Arg Asp Pro His Arg His Glu
            35                  40                  45

Leu Arg Ser Tyr Arg Ile Val Asp Gly Ala Val Thr
    50                  55                  60
```

<210> SEQ ID NO 18
<211> LENGTH: 58
<212> TYPE: PRT
<213> ORGANISM: Escherichia coli

<400> SEQUENCE: 18

```
Ile Lys Ile Asn Ala Ser Ala Leu Ile Leu Ala His Asn His Pro Ser
1               5                   10                  15

Gly Cys Ala Glu Pro Ser Lys Ala Asp Lys Leu Ile Thr Glu Arg Ile
            20                  25                  30

Ile Lys Ser Cys Gln Phe Met Asp Leu Arg Val Leu Asp His Ile Val
            35                  40                  45

Ile Gly Arg Gly Glu Tyr Val Ser Phe Ala
    50                  55
```

<210> SEQ ID NO 19
<211> LENGTH: 57
<212> TYPE: PRT
<213> ORGANISM: Drosophila melanogaster

<400> SEQUENCE: 19

```
Thr Gly Arg Pro Glu Met Val Val Gly Trp Tyr His Ser His Pro Gly
1               5                   10                  15

Phe Gly Cys Trp Leu Ser Gly Val Asp Ile Asn Thr Gln Gln Ser Phe
            20                  25                  30
```

-continued

```
Glu Ala Leu Ser Glu Arg Ala Val Ala Val Val Val Asp Pro Ile Gln
            35                  40                  45

Ser Val Lys Gly Lys Val Val Ile Asp
        50                  55

<210> SEQ ID NO 20
<211> LENGTH: 57
<212> TYPE: PRT
<213> ORGANISM: Homo sapiens

<400> SEQUENCE: 20

Thr Gly Arg Pro Glu Met Val Val Gly Trp Tyr His Ser His Pro Gly
1               5                   10                  15

Phe Gly Cys Trp Leu Ser Gly Val Asp Ile Asn Thr Gln Gln Ser Phe
            20                  25                  30

Glu Ala Leu Ser Glu Arg Ala Val Ala Val Val Val Asp Pro Ile Gln
            35                  40                  45

Ser Val Lys Gly Lys Val Val Ile Asp
        50                  55

<210> SEQ ID NO 21
<211> LENGTH: 57
<212> TYPE: PRT
<213> ORGANISM: Dictyostelium discoideum

<400> SEQUENCE: 21

Thr Gly Arg Asp Glu Ile Val Ile Gly Trp Tyr His Ser His Pro Gly
1               5                   10                  15

Phe Gly Cys Trp Leu Ser Ser Val Asp Val Asn Thr Gln Gln Ser Phe
            20                  25                  30

Glu Gln Leu Gln Ser Arg Ala Val Ala Val Val Val Asp Pro Leu Gln
            35                  40                  45

Ser Val Arg Gly Lys Val Val Ile Asp
        50                  55

<210> SEQ ID NO 22
<211> LENGTH: 57
<212> TYPE: PRT
<213> ORGANISM: Saccharomyces cerevisiae

<400> SEQUENCE: 22

Thr Gly Arg Asp Gln Met Val Val Gly Trp Tyr His Ser His Pro Gly
1               5                   10                  15

Phe Gly Cys Trp Leu Ser Ser Val Asp Val Asn Thr Gln Lys Ser Phe
            20                  25                  30

Glu Gln Leu Asn Ser Arg Ala Val Ala Val Val Val Asp Pro Ile Gln
            35                  40                  45

Ser Val Lys Gly Lys Val Val Ile Asp
        50                  55
```